United States Patent
Cosgrove et al.

[19]

[11] Patent Number: 6,162,172
[45] Date of Patent: *Dec. 19, 2000

[54] METHODS AND APPARATUS FOR RETRACTING TISSUE

[75] Inventors: Delos M. Cosgrove, Hunting Valley, Ohio; Norma L. Lowe, Fullerton, Calif.; Keith Myers, Lake Forest, Calif.; Richard Rhee, Diamond Bar, Calif.

[73] Assignee: Edwards Lifesciences Corporation, Irvine, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/016,489

[22] Filed: Jan. 30, 1998

[51] Int. Cl.$^7$ .................................................. A61B 17/00
[52] U.S. Cl. ........................... 600/208; 600/235; 600/245
[58] Field of Search .................................... 600/201, 202, 600/206, 208, 235, 245, 210, 209, 212, 237, 238, 236; 606/191

[56] References Cited

U.S. PATENT DOCUMENTS

| | | | |
|---|---|---|---|
| 2,812,758 | 11/1957 | Blumenschein | 600/208 |
| 3,888,117 | 6/1975 | Lewis | 600/202 X |
| 4,387,706 | 6/1983 | Glass | 600/236 X |
| 4,782,820 | 11/1988 | Woods | 600/208 |
| 5,159,921 | 11/1992 | Hoover | 600/208 X |
| 5,179,938 | 1/1993 | Lonky | 600/223 |
| 5,318,011 | 6/1994 | Federman et al. | 600/236 |
| 5,374,272 | 12/1994 | Arpa et al. | 600/236 X |
| 5,651,762 | 7/1997 | Bridges | 600/208 X |
| 5,795,290 | 8/1998 | Bridges | 600/208 X |
| 5,810,721 | 9/1998 | Mueller et al. | 600/208 X |
| 5,851,177 | 12/1998 | Koch | 600/206 |
| 5,865,729 | 2/1999 | Meechan et al. | 600/245 X |
| 5,879,290 | 3/1999 | Bridges et al. | 600/206 |
| 5,976,078 | 11/1999 | Bridges | 600/235 X |
| 6,063,025 | 5/2000 | Bridges et al. | 600/208 |

FOREIGN PATENT DOCUMENTS

| | | | |
|---|---|---|---|
| 263211 | 8/1913 | Germany | 600/238 |
| 114051 | 3/1918 | United Kingdom | 600/236 |

*Primary Examiner*—Jeffrey A. Smith
*Attorney, Agent, or Firm*—Eric K. Satermo; James W. Inskeep; Guy L. Cumberbatch

[57] ABSTRACT

Surgical apparatus and associated methods of use are provided for retracting tissue around an incision. The apparatus includes a member having an inner peripheral surface and an outer peripheral surface. An adjustable aperture is definable within the inner peripheral surface as the member is adjusted between a compressed condition in which the aperture is substantially closed and an expanded condition in which the aperture is substantially open. The apparatus is positioned within a surgical incision in the compressed condition, and is adjusted to the expanded condition in situ to define an opening within the incision through the aperture whereby a surgical field may be viewed and/or accessed.

93 Claims, 7 Drawing Sheets

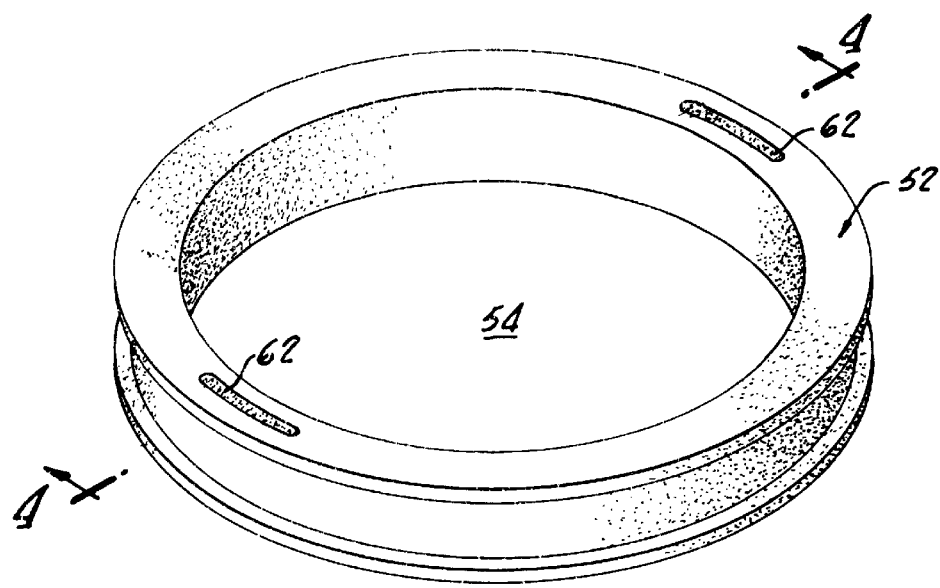
_Fig. 1._
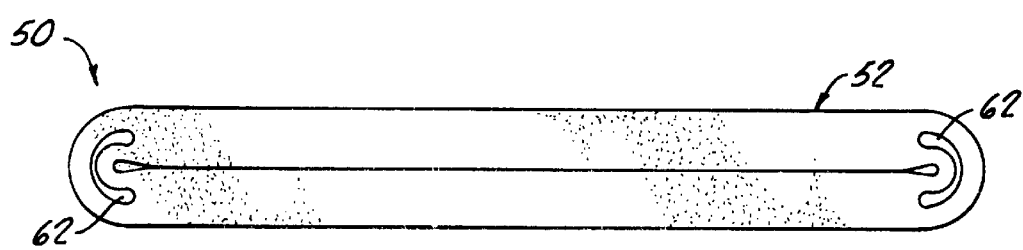
_Fig. 2._
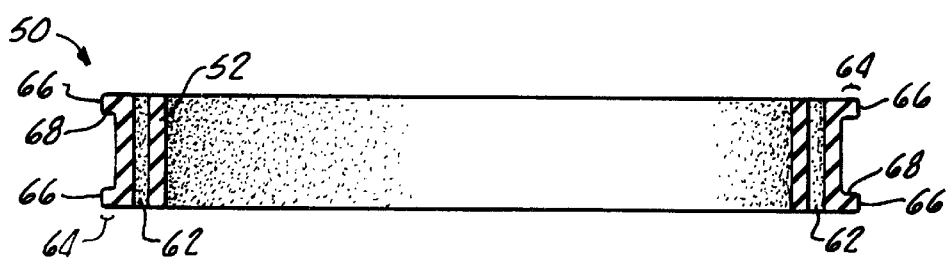
_Fig. 4._

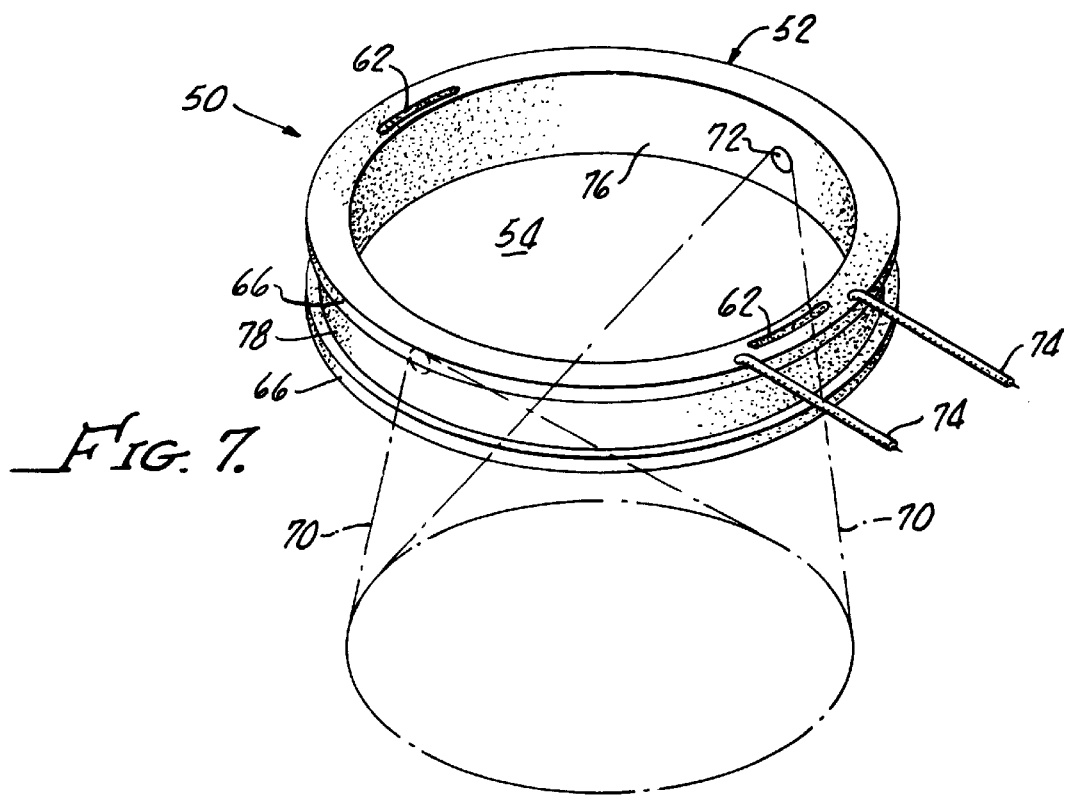
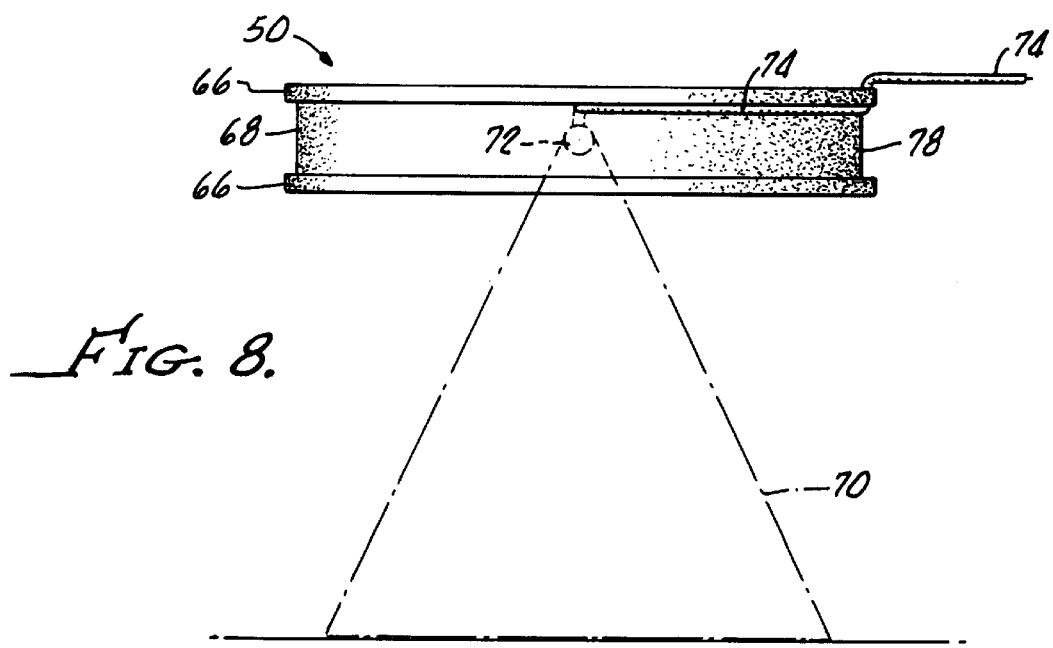

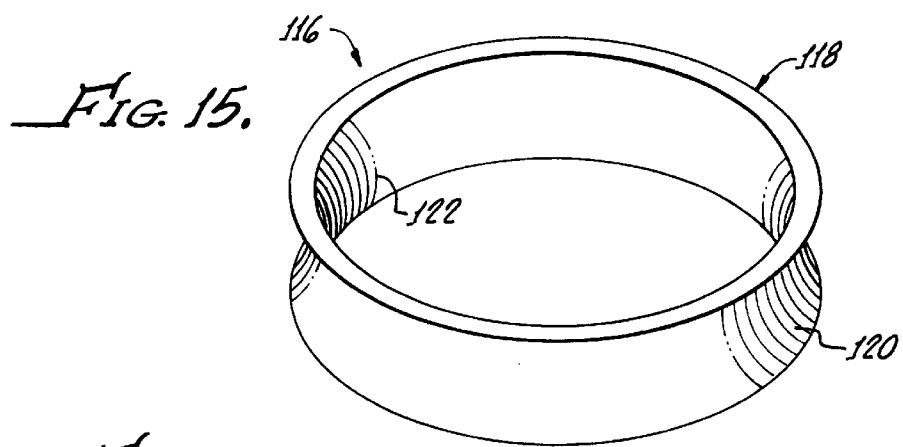
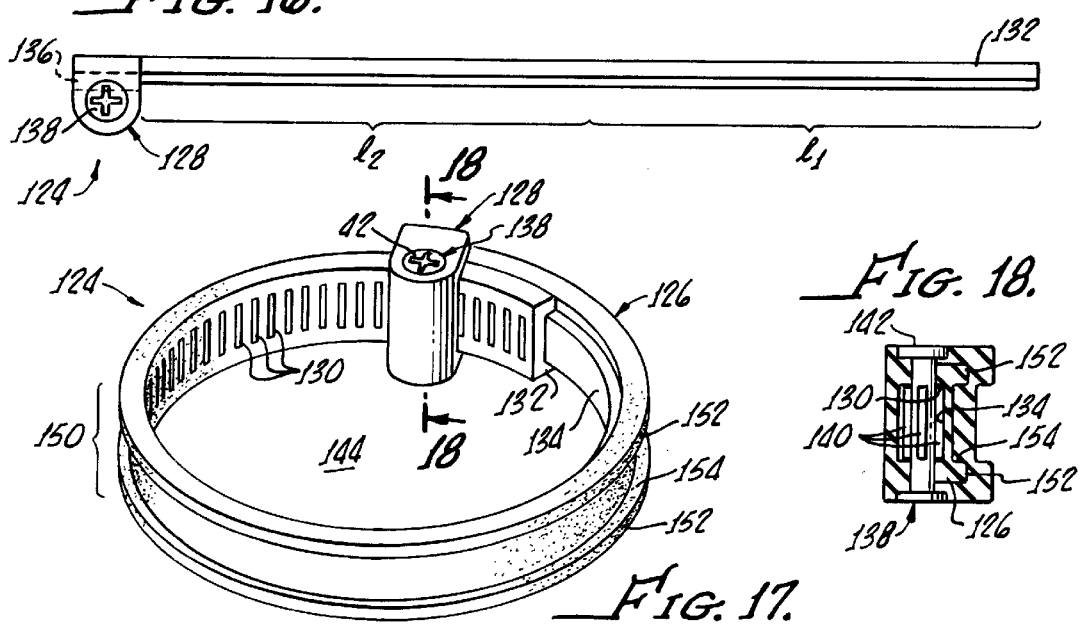
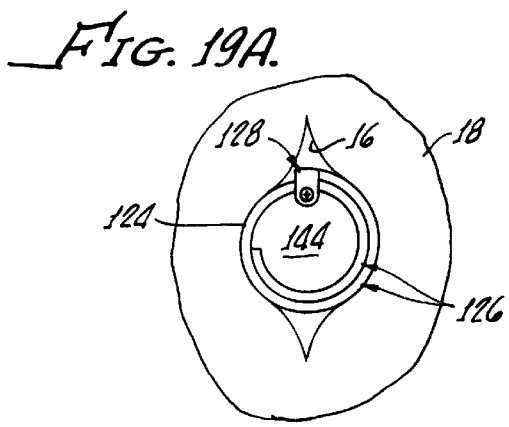 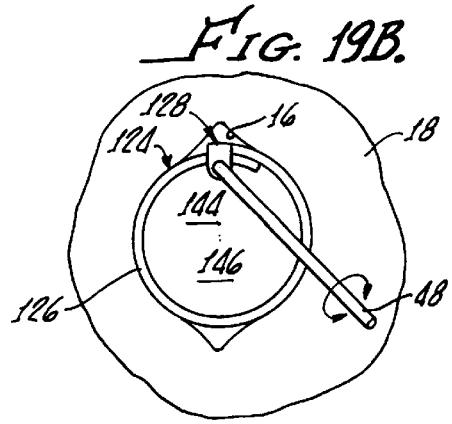

METHODS AND APPARATUS FOR RETRACTING TISSUE

FIELD OF THE INVENTION

The present invention is directed to surgical apparatus and associated methods for retracting tissue during surgical procedures. More particularly, the present invention is directed to simplified, in situ surgical retracting apparatus and methods for their use within restricted surgical fields or in connection with delicate animal tissue where traditional retracting devices are unwieldy or unsuitable.

BACKGROUND OF THE INVENTION

Surgical apparatus for retracting animal tissue during invasive surgical procedures are well known in the art. In their most simple form, surgical retractors can comprise a hand-held device, typically made of surgical-grade stainless steel or other rigid material, having tissue-engaging projections which the surgeon or surgical assistant utilizes to engage and displace tissue manually from the surgical field of operation. More complex retracting devices include parallel tissue engaging appendages projecting from scissor-like or screw-jack structures which can be adjusted by the surgeon to separate the tissue-engaging paddles from one another after they have been inserted into a surgical incision. As those skilled in the art appreciate, the projecting scissor- or screw-adjusting structures must be sufficiently large to allow the tissue-contacting projections or jaws to open sufficiently in order to facilitate surgical access to the field of operation. Whether manipulated by hand or adjusted in place, these prior art surgical retracting apparatus all include bulky structures projecting out from the surgical field within the patient's body. One of the most dramatic examples of such a medical device is the surgical retractor used for "cracking the chest" during open heart surgery where the patient's rib cage is separated at the sternum and held open by the retractor while the surgeon or surgical team accesses the patient's heart.

Recently, advancing trends in medical practice have lead to the development of "minimally invasive" surgical procedures designed to reduce or substantially eliminate the majority of physical trauma experienced by the patient. An exemplary minimally invasive procedure is the limited or "minithoracotomy" wherein one or more small incisions are made in the rib cage rather than splitting the patient's chest open. In such a minimally invasive approach, smaller external retractors are positioned within the incisions and mechanically opened to separate the chest wall tissue and provide access to the interior chest cavity and the heart. The surgeon is then able to make incisions in the heart tissue in order to provide access to internal heart structures.

Surgery upon the heart itself is illustrative of the drawbacks associated with conventional, prior art surgical retractors. Because of their relatively bulky projecting operating structures, conventional retractors are not well suited for use within the crowded confines of small, minimally invasive surgical incisions. Even hand-held retractors require the projecting manipulating handles to extend through the incision which further reduces the space available for surgical operation while obstructing visual access to the surgical field. As a result, conventional approaches to retraction of heart tissue itself typically involve temporarily sewing the heart tissue encroaching on the incision to adjacent tissue within the chest cavity and drawing the sutures tight to hold the encroaching tissue out of the way. Upon completion of the surgical procedure, the securing sutures are removed to allow the tissue to return to its normal position where the incision can be closed permanently. Compounding matters, surgical procedures executed deep within the heart, such as a mitral valve replacement, are difficult to visualize due to inadequate lighting. Unlike conventional open heart surgery where the heart is exposed to ambient lighting and external spot sources of light, minimally invasive procedures provide access to the interior of the heart through relatively narrow channels which are difficult to illuminate, particularly with conventional retractors in place.

Accordingly, in view of the foregoing, it is an object of the present invention to provide surgical apparatus and associated methods of use for retracting tissue which eliminate many of the drawbacks associated with prior art surgical retractors.

It is an additional object of the present invention to provide such surgical apparatus and methods for retracting tissue which atraumatically provide the surgeon with unobstructed access and enhanced viewing of the surgical field.

It is yet another object of the present invention to provide surgical apparatus for retracting tissue which do not require bulky external handles or projecting operating mechanisms.

SUMMARY OF THE INVENTION

These and other objects are achieved by the surgical apparatus and associated methods of the present invention which retract animal tissue (human, mammalian or otherwise) in an atraumatic, non-obstructive manner. In a broad aspect, the surgical apparatus for retracting animal tissue includes a member having a loop shape which may be either open or closed. The loop-shaped member has an inner periphery defining an interior surface and an outer periphery defining an exterior surface. The inner peripheral surface defines an aperture through which surgical access and viewing are achieved. The member itself is adjustable between a compressed condition in which the aperture is substantially closed and an expanded condition in which the aperture is open and the surrounding tissue is retracted or displaced out of the way. The member may be resiliently deformable and biased to the open, expanded condition or it may be provided with a mechanical adjuster. In the resiliently deformable embodiment of the present invention, the member may be constructed to be sufficiently flexible to enable opposing portions of the interior surface to be brought into contact with each other when the member is fully compressed, for example, by the surgeon's hand. To assist in this functionality or to focus the stresses within the compressed member, portions of the member may be provided with one or more flex portions having less resiliency than the remaining portions of the member. Exemplary flex portions include notches, slots, creases and equivalent permanent deformations in the member. Alternatively, materials having relatively enhanced flexibility may be incorporated directly into the member to form the flex portions. Those skilled in the art will appreciate that flex portions may be provided in both the open- and closed-loop embodiments of the present invention.

Alternatively, where it is desired to provide the member with a mechanical adjuster it is preferred that the member be of the open-loop configuration. This configuration will result in the member having opposing ends. In the exemplary embodiment of the present invention illustrated herein, the first end of the member is slidably received in a slot provided on the second end thereof Further, the second end is provided with mechanical adjuster which allows the surgeon to precisely control the degree of compression or expansion provided by the surgical apparatus. This can be accomplished by utilizing a rotatable toothed mechanical adjuster which engages corresponding notches or teeth formed along a first length of member adjacent to the first end. These teeth can be formed on the inner peripheral surface or along edge surfaces of the member.

As an additional feature of the present invention, the loop-shaped member may be provided with a variety of tissue-engaging structures. Preferably, these are formed or disposed upon the outer peripheral surface of the member. Exemplary tissue-engaging structures include projecting annular ridges or depressed grooves formed in the outer periphery of the member. These structures aid in retaining the position of the surgical apparatus within an incision by more positively engaging the tissue surfaces defined by the incision as the radially outwardly directed force of the expanded member is directed into the displaced animal tissue.

To utilize the surgical apparatus of the present invention as a tissue retractor in accordance with the teachings thereof, the surgeon or operator simply forms an incision in the patient's tissue and positions the surgical apparatus in its compressed, insertion position within the incision. The apparatus is then expanded to the tissue-supporting condition either through its own, intrinsic resilient biasing or through precise mechanical adjustment. Once expanded, the interior peripheral surface of the member defines an open, access aperture through which additional surgical instruments or devices may be inserted while the surgical field is open to view. Those skilled in the art will appreciate that the unique configuration of the surgical apparatus of the present invention provides maximal visualization and access to the surgical field through the complete elimination of projecting operating structures such as handles, transverse scissors and screw jacks. Removal of the apparatus is equally simple involving the manual or mechanical compression of the member to its collapsed or closed position which disengages the outer peripheral surface or tissue-engaging structure from the surrounding tissue of the incision so that the apparatus can be withdrawn.

It will also be appreciated by those skilled in the art that the closed-loop embodiment of the present invention can be configured in various intended expanded diameters as appropriate for the intended surgical procedures. For example, mitral valve surgery may involve an expanded diameter on the order of two or three centimeters. Alternatively, abdominal surgery may require a significantly larger expanded diameter. Similarly, the resiliency of the deformable, closed-loop embodiment can be modified for compatibility with the intended animal tissue. For example, retracting muscle tissue may require a significantly more resilient apparatus than would be desirable for retracting brain tissue. Similar sizing and resiliency concerns are appropriate for the open-loop member configuration of the present invention as well. However, where the open-loop embodiment is provided with a mechanical adjuster, the ability to precisely control the expanded diameter may address this need.

Additionally, the surgical apparatus may be provided with additional features including self-contained or directed light sources or surgical instrument retainers. For example, light-emitting elements coupled to an external power source may be incorporated into the member. Alternatively, chemiluminescent light sources may be incorporated. For example, the member may be formed with first and second chamber divided by a rupturable structure. At least one of the chambers would include a translucent wall defining at least a portion of the inner periphery of the member. Individual components of a chemiluminescent system as known in the art may be incorporated in each of the first and second chambers. As a result, when the surgical apparatus is compressed, the rupturable structure is broken, allowing the chemiluminescent chemical components to mix and generate light.

To assist the surgeon utilizing the surgical apparatus of the present invention by retaining additional surgical apparatus, instruments, sutures, or the like, the member may be provided with one or more retaining structures. These can include resiliently deformable slots, grooves or projections into which various surgical devices can be temporarily fixed. In this manner, the operating surgeon can utilize the apparatus of the present invention to maintain control of multiple surgical instruments while providing clear access to the surgical field.

Other aspects, features, and advantages of the present invention will become apparent to those persons having ordinary skill in the art to which the present invention pertains from the following description taken in conjunction with the accompanying drawings.

BRIEF DESCRIPTION OF THE DRAWINGS

FIG. 1 is a perspective view of an exemplary tissue surgical apparatus illustrating the principles of the present invention;

FIG. 2 is a view of the exemplary tissue apparatus of FIG. 1 in a compressed condition;

FIG. 4 is a cross-sectional view of the exemplary apparatus of FIG. 1, taken along line 4—4, illustrating particular features of the apparatus, including exemplary tissue-engaging structures and flex portions;

FIG. 7 is a perspective view an alternative exemplary embodiment of the apparatus of the present invention illustrating an exemplary light source;

FIG. 8 is a side view of the apparatus of FIG. 7;

FIG. 15 is a perspective view of another exemplary alternative embodiment of the apparatus of the present invention;

FIG. 16 is a schematic view of an open loop apparatus additionally provided with a mechanical adjuster;

FIG. 17 is a perspective view of the apparatus of FIG. 16;

FIG. 18 is a cross-sectional view of the apparatus of FIG. 17, taken along line 18—18 and particularly illustrating an exemplary mechanical adjuster;

FIGS. 19A and 19B are schematic views illustrating steps of an exemplary method of retracting tissue in a surgical procedure utilizing the apparatus of FIG. 16;

DETAILED DESCRIPTION OF EXEMPLARY EMBODIMENTS

Referring to FIG. 1 of the drawings, an exemplary embodiment of the surgical apparatus 50 of the present invention is illustrated. Apparatus 50 includes a member 52 with an aperture 54 defined therein. Apparatus 50 is expandable and is shown in an expanded condition in FIG. 1. Alternatively, apparatus 50 may be thought of as being compressible, with the apparatus shown in a compressed condition in FIG. 2. Expandable or compressible, in either case the deformable or shape-transformable apparatus 50 is adjustable or positionable in a state or condition in a range defined by the expanded condition of FIG. 1 and the compressed condition of FIG. 2. As shown, aperture 54 is substantially open when apparatus 50 is in an expanded condition and substantially closed when apparatus 50 is in a compressed condition. According to an exemplary embodiment of apparatus 50, member 52 is made from resilient bio-compatible material such that apparatus 50 is biased to return to the expanded condition from a compressed condition. That is, when compressed, member 52 may apply force radially in an outward direction. An exemplary configuration of member 52 in a closed-loop shape through an open-loop configuration is within the scope of the present invention.

Figure 3A:
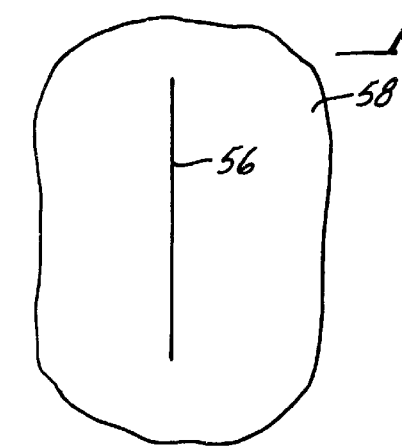
FIGS. 3A, 3B, and 3C are sequential schematic views illustrating a surgical procedure for retracting tissue in accordance with the present invention.
Figure 3B:
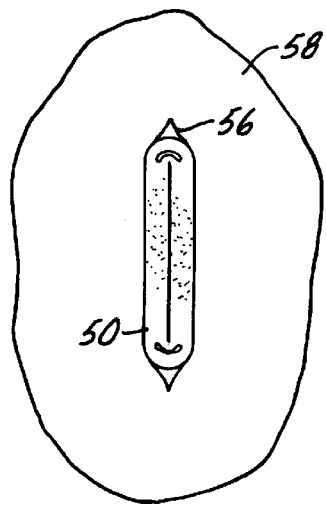
Figure 3C:
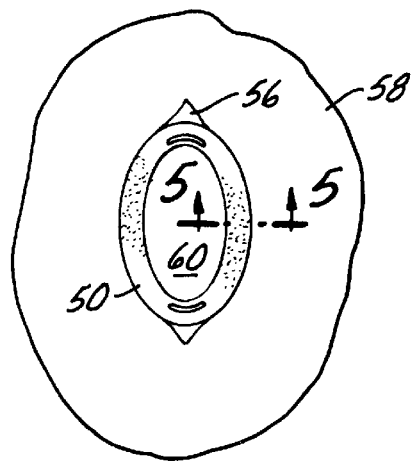

FIGS. 3A–3C illustrate an exemplary method of utilizing apparatus 50 to retract tissue in a surgical procedure. After an incision 56 is made in tissue 58 as shown in FIG. 3A, apparatus 50 may be inserted into and/or positioned within incision 56 while in a compressed condition, as shown in FIG. 3B. Once in position, apparatus 50 may then be expanded to an expanded condition within incision 56, thereby urging tissue 58 apart and opening incision 56. This expansion of apparatus 50 may be accomplished by releasing apparatus 50 with, for example, forceps. By such an expansion, an opening 60 is defined by the opened incision 56 within the now retracted tissue 58 and by aperture 54 of apparatus 50. Accordingly, a surgeon has unobstructed vision and access to the surgical field and may perform a surgical procedure through opening 60. As shown in FIG. 3C, during use, apparatus 50 need not take a substantially non-compressed shape (as shown in FIG. 1) but need only take a shape in which aperture 54 is not entirely closed so that opening 60 is definable and available for further surgical steps.

Figure 5:
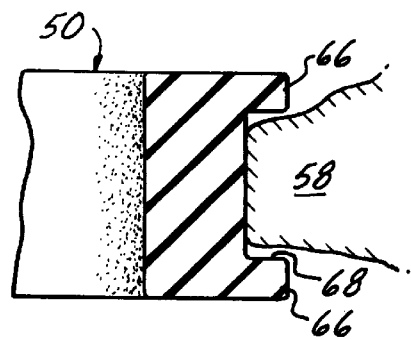
FIG. 5 is an enlarged fragmentary cross-sectional view of the exemplary apparatus taken along line 5—5 of FIG. 3C, particularly illustrating the exemplary tissue-engaging structure.

With further reference to FIGS. 1 and 2, according to an exemplary embodiment of apparatus 50, member 52 may have flex portions 62 formed therein to facilitate the compression of apparatus 50. Flex portions 62 are preferably configured as portions of member 52 having less resiliency or elasticity than other portions of member 52. For example, as particularly shown in FIG. 4, flex portions 62 may be configured as slots within member 52, specifically axial slots. Accordingly, when apparatus 50 is compressed, member 52 folds outwardly at flex portions 62 rather than at some other location along member 52. As illustrated, it is preferable to form a pair of diametrically opposed flex portions 62 in member 52 so that apparatus 50 is compressible to the compressed condition shown in FIG. 2 in which apparatus 50 is substantially flattened, oblong, or elliptical in shape, With continued reference to FIGS. 1 and 4 and additional reference to FIG. 5, apparatus 50 may be configured with tissue-engaging structure 64 for engaging the tissue 58 exposed by and surrounding an incision 56 to aid in retaining apparatus 50 in position within the incision. In accordance with an exemplary embodiment of the invention, tissue-engaging structure 64 includes ridges 66 formed on an outer surface of member 52. A channel 68 is defined between ridges 66. With the provision of tissue-engaging structure 64, apparatus 50 may be positioned within an incision so that tissue 58 is substantially engaged by tissue-engaging structure 64, with the tissue 58 received within channel 68 and retained by ridges 66. Accordingly, tissue-engaging structure 64 augments the outward radial resiliency of member 52 in retaining apparatus 50 within an incision.

Figure 6:
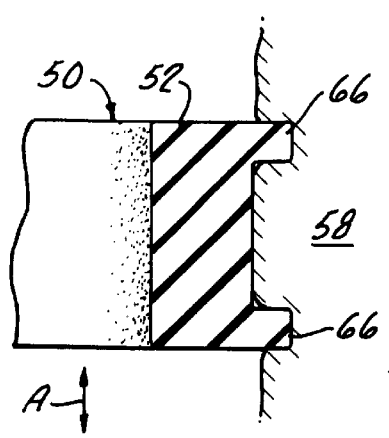
FIG. 6 is an enlarged fragmentary cross-sectional view similar to that of FIG. 5, showing the exemplary tissue-engaging structure of the apparatus in an alternative surgical procedure.

Alternatively, referencing FIG. 6, if apparatus 50 is positioned within an incision made in relatively thick tissue (that is, in tissue having a thickness greater than a thickness of channel 68), tissue-engaging structure 64 may still aid in retaining apparatus 50 within the incision by engaging with the surface of the tissue 58. Because of the expandable characteristics of apparatus 50, ridges 66 are urged against the tissue 58, thereby retarding or preventing movement of apparatus 50 in the axial direction shown by arrow A. To reduce or eliminate the risk of injuring the tissue 58, tissue-engaging structure 64 is preferably configured as atraumatic as possible while still retaining tissue-engaging characteristics.

Apparatus 50 may be configured in any desired shape. In the exemplary embodiment shown in FIGS. 1–6, apparatus 50 is substantially cylindrical when in the expanded condition. However, apparatus 50 may be configured so as to be elliptical or ovoid when in the expanded condition. Alternatively, apparatus 50 may be configured to assume an irregular configuration specifically designed for a particular type of incision or surgical application. In the cylindrical embodiment of apparatus 50, ridges 66 of tissue-engaging structure 64 are in the form of annular extensions of end surfaces of member 52.

Referencing FIGS. 7 and 8, apparatus 50 may include a light source for providing light 70 to a surgical field. Many surgical procedures in which apparatus 50 may be applied are in remote or awkward locations in the body. Accordingly, light sources external to the body in the surgical theater may not illuminate the entire surgical field or may cast distracting shadows. The provision of the light source on apparatus 50 itself, which is essentially adjacent to or directly above the surgical field, substantially eliminates any shadows or non-illuminated areas within the surgical field.

The exemplary light source illustrated in FIGS. 7 and 8 includes a light-emitting element 72 coupled to a lead 74. In accordance with an exemplary embodiment, a plurality of light-emitting elements 72 may be spaced around an inner periphery 76 of member 52. Providing a plurality of spaced light-emitting elements 72 eliminates any shadows which may be created by surgical instruments or other apparatus positioned within the surgical field through aperture 54 of apparatus 50. Leads 74 may be secured to member 52 through, for example, ridges 66, with leads 74 being disposed in channel 68 on an outer periphery 78 of member 52 as shown in FIG. 8. Leads 74 may then be attached to electronics within the surgical theater to provide power to light-emitting elements 72. Leads 74, as well as light-emitting elements 72, are configured on member 52 so as to minimize the effect of compressing apparatus 50; for example, leads 74 may be attached to member 52 near ends of flex portion 62 as shown in FIG. 7. Leads 74 may be electrical conductors, fiber optics, or other suitable media. If leads 74 are configured as fiber optics, light-emitting elements 72 are defined as the end of the fiber optics from which light is emitted.

Figure 9:
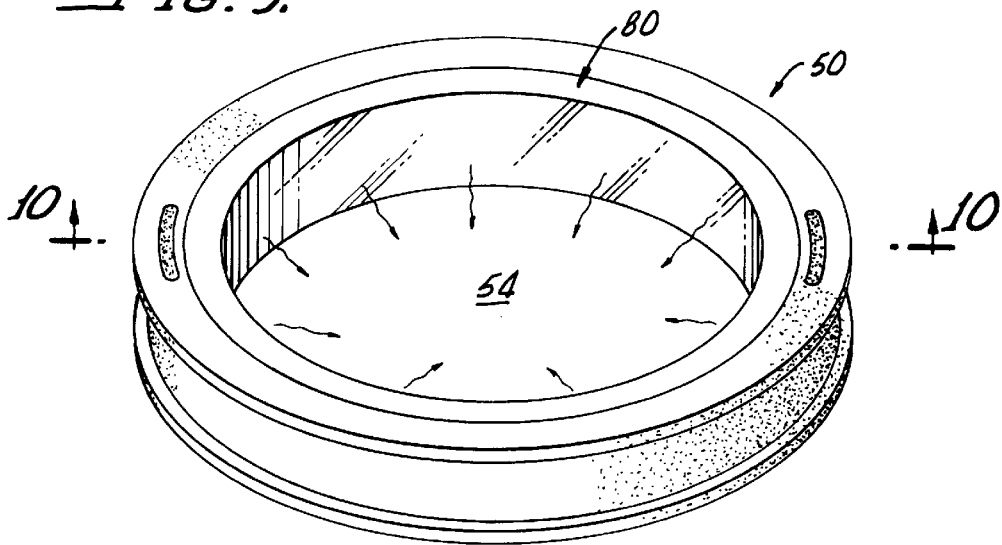
FIG. 9 is a perspective view of an alternative apparatus of the present invention, particularly illustrating an additional exemplary light source.
Figure 10:
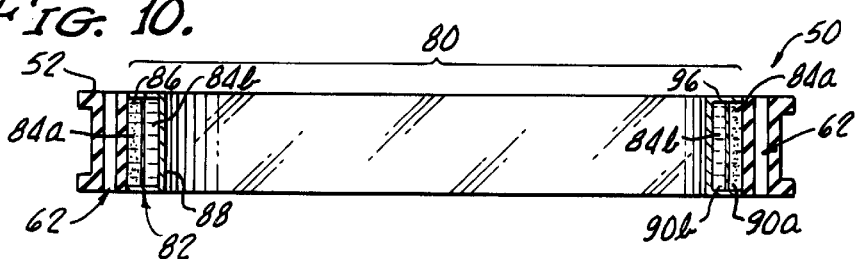
FIG. 10 is a cross-sectional view of the apparatus of FIG. 9 taken along line 10—10.

An alternative embodiment of the light source is exemplified in FIG. 9, in which a light-emitting element is configured as a luminescent structure 80 disposed within an inner periphery of member 52. As shown in FIG. 10, luminescent structure 80 preferably includes a twin-chambered housing 82 having first and second chambers 84*a*, 84*b* divided by a breakable, rupturable, or piercable divider 86. Luminescent structure 80 has a translucent inner peripheral wall 88. First and second chambers 84*a*, 84*b* respectively contain first and second chemical solutions 90*a*, 90*b* which, when mixed together, generate light through chemiluminescence.

Figure 11A:
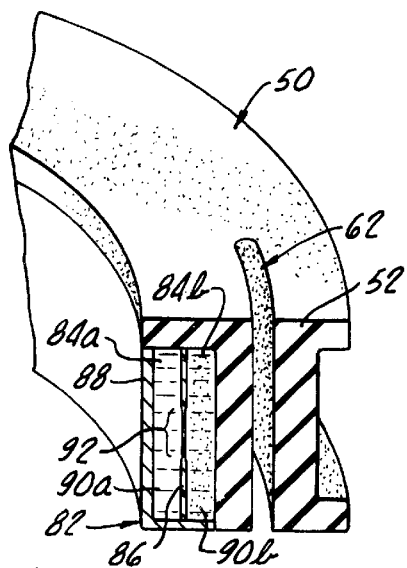
FIGS. 11A and 11B are enlarged fragmentary cross-sectional views of the apparatus of FIG. 9, respectively illustrating the apparatus in an expanded condition and in a compressed condition and the associated action of an exemplary chemiluminscent light source.
Figure 11B:
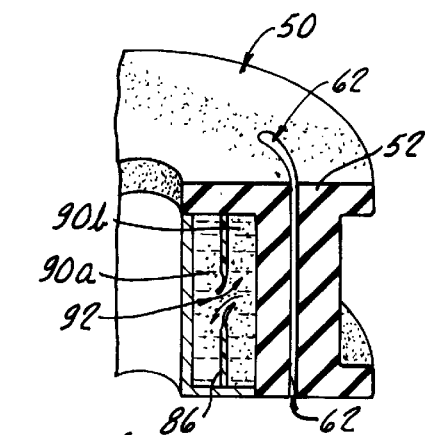

FIG. 11A shows an enlarged sectional view of apparatus 50 in an expanded condition with divider 86 in tact. To activate chemiluminescence, divider 86 is punctured, preferably when apparatus 50 is compressed as shown in FIG. 11B (also see FIG. 2 for reference of a compressed condition), allowing first and second chemical solutions 90*a*, 90*b* to mix. The mixing of chemical solutions 90*a*, 90*b* may be facilitated by agitating apparatus 50. Apparatus 50 may then be positioned within an incision as described above and shown in FIGS. 3B and 3C. When expanded, light generated by the chemiluminescence illuminates the surgical field through aperture 54. The puncturing or breaking of divider 86 may be accomplished by a physical structure disposed within housing 82 or by the increased pressure of chemical solutions 90*a*, 90*b* against divider 86 caused by the compression of apparatus 50. As compared to the use of the previously described light-emitting apparatus, luminescent structure 80 is self-contained and does not require external manipulation or power sources for light generation once apparatus 50 is positioned within an incision.

In accordance with an exemplary embodiment of luminescent structure 80, divider 86 may have a break point or portion 92 near flex portions 62 to facilitate the piercing or breaking of divider 86 when apparatus 50 is compressed as shown in FIGS. 11A and 11B. Break portion 92 may be defined by a thinned portion of divider 86. In addition, it may be preferable to extend translucent inner peripheral wall 88 over a bottom end portion 94 of housing 82 so that light is directed to the surgical field through end portion 94. In some applications, it may be preferable to have a high opacity of top end portion 96 of housing 82 so that light is not directed toward the surgeon. Further, inner peripheral wall 88 may be configured so that light is directed only substantially downward toward the surgical field by, for example, an internal louver arrangement. A commercial supplier of chemiluminescent structures is Omniglow Corporation of Novato, Calif., which produces non-toxic light structures under the name of CYALUME® which radiate light in more than one color for durations on the order of eight hours.

Figure 12:
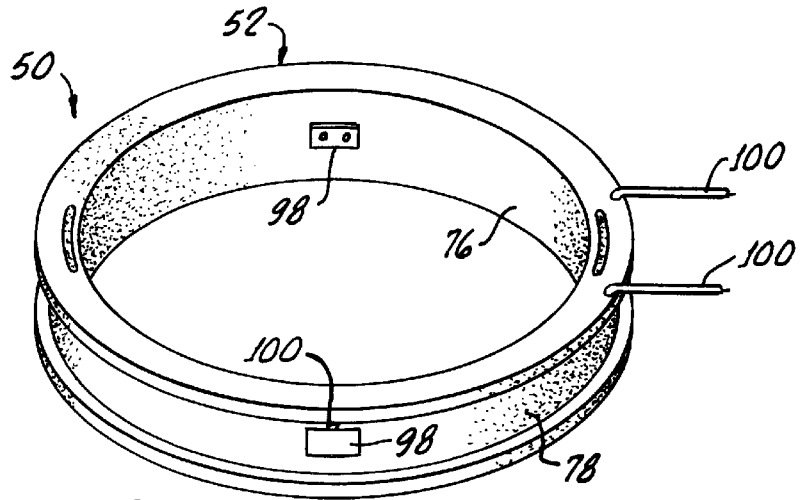
FIG. 12 is a perspective view of an additional exemplary embodiment of the apparatus of the present invention, particularly illustrating a sensing apparatus.

Yet another exemplary embodiment of apparatus 50 is illustrated in FIG. 12 in which monitoring or sensing apparatus 98 coupled to leads 100 is disposed on member 52. Leads 100 may be connected with electrical equipment in the surgical theater for carrying electrical signals between sensing apparatus 98 and the external equipment. Sensing apparatus 98 may carry out diagnostic functions and may include, for example, heat sensors for monitoring a temperature in the surgical field. Sensing apparatus 98 may also include video-monitoring equipment to provide a video image of the surgical field. Sensing apparatus 98 may be configured within member 52 such that individual elements of the sensing apparatus are disposed on either the inner or the outer peripheral surface 76 or 78 of member 52 as shown. An alternative to physical leads 100 may be a wireless communication configuration in which sensing apparatus 98 includes a transmitter and/or a receiver for communicating with electrical equipment by means of electromagnetic waves. Such a wireless embodiment eliminates any unnecessary and possibly obstructive electrical leads in the surgical field.

Figure 13:
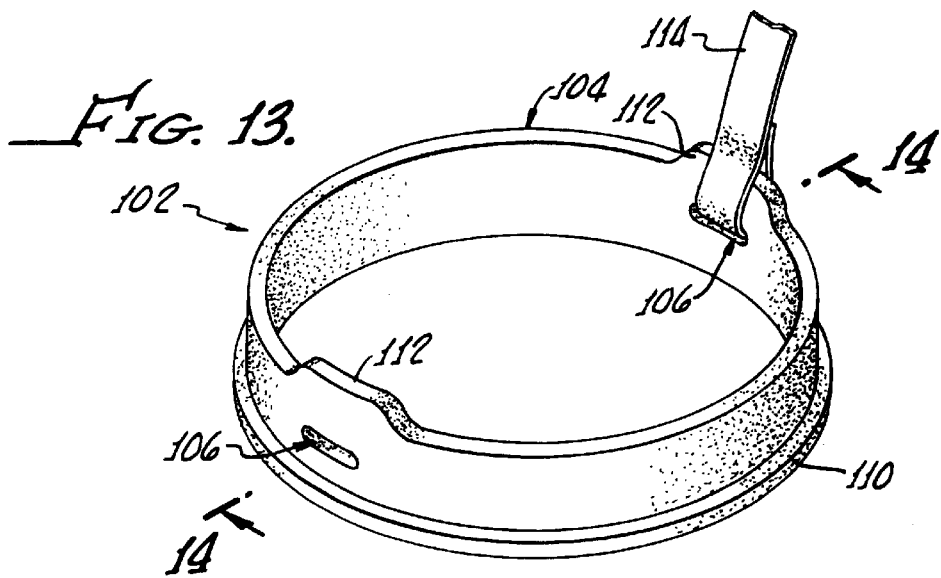
FIG. 13 is a perspective view of an additional exemplary apparatus of the present invention.
Figure 14:
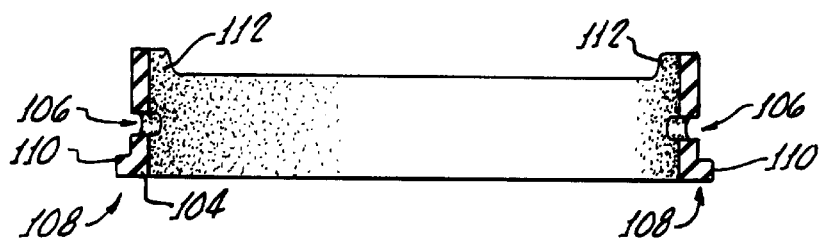
FIG. 14 is a cross-sectional view of the apparatus of FIG. 13 taken along line 14—14.

With reference to FIGS. 13 and 14, apparatus 102 of the present invention is exemplified in an alternative embodiment. Apparatus 102, like apparatus 50 illustrated above, includes a member 104. Flex portions 106 are formed in member 104 to facilitate the compression of apparatus 102. However, rather than forming axial slots within the member of the surgical apparatus as described above, flex portions 106 in accordance with this embodiment are formed as radial slots in member 104. Alternatively, notches or cavities may be formed in place of slots. Apparatus 102 may also include tissue-engaging structure 108 comprised of an annular ridge 110 and axial projections 112. Annular ridge 110 functions analogously to ridges 66 described above. Axial projections 112 provide an increased outer annular surface area for engaging tissue of an incision, and facilitate the removal of apparatus 102 from an incision by providing an element onto which forceps or hemostats may grasp. Alternatively, apparatus 102 may include a tab 114 to facilitate the removal of apparatus 102 from an incision with forceps or hemostats. Tab 114, which is preferably flexible, may be attached to apparatus 102 through a slot of flex portion 106.

Yet another embodiment of the tissue surgical apparatus 116 of the present invention is shown in FIG. 15. Like apparatus 50 described above, surgical apparatus 116 is compressible and, accordingly, expandable. Apparatus 116 includes a member 118 which is configured to have a concave outer annular periphery 120 which functions as tissue-engaging means as described above. Such a concave configuration is substantially atraumatic and does not necessarily have flex portions to facilitate the compressing of apparatus 116. An inner periphery 122 of member 118 may be substantially cylindrical or, as shown, convex.

With reference to FIGS. 16, 17, and 18, a fiurther exemplary embodiment of a tissue surgical apparatus 124 according to the principles of the present invention is shown. Apparatus 124 includes a member 126 and an adjusting portion 128 attached to an end of member 126 for expanding and for compressing apparatus 124. A plurality of slots or notches 130 are formed in an inner periphery 132 along a first length $l_1$ of member 126, and an elongate projection 134 is formed on inner periphery 130 along a second length $l_2$ of member 126 (which will be discussed below). Adjusting portion 128 includes a slot 136 for slidably receiving the first length $l_1$ of member 126, and a rotatable drive 138 for driving the first length $l_1$ of member 126 through slot 136. Drive 138 has teeth 140 for engaging or meshing with notches 130 of member 126, and a head 142 for allowing a physician to actuate drive 138. An aperture 144 is defined within member 126 when the first length $l_1$ of member 126 is received in slot 136.

FIGS. 19A and 19B illustrate apparatus 124 utilized in a surgical procedure. As shown in FIG. 19A, apparatus 124 is positioned within an incision 56 made in tissue 58 while in a compressed condition. Apparatus 124 is then expanded to an expanded condition, as shown in FIG. 19B, thereby retracting tissue 58 and defining an opening 146 within member 126 through which the surgical field may be viewed. The expansion of apparatus 124 may be accomplished by the surgeon engaging head 142 with a complementary surgical implement 148 and rotating drive 138. Teeth 140 mesh with notches 130 as drive 138 is rotated, as shown in FIG. 18. After the surgical procedure is completed, apparatus 124 may then be compressed for removal from incision 56. An example of one of the alternatives to the arrangement of teeth 140 and notches 130 is configuring drive 138 with a worm gear.

With further reference to FIGS. 17 and 18, apparatus 124 may include tissue-engaging structure formed on an outer periphery of member 126. As described above in relation to the exemplary embodiment illustrated in FIGS. 5 and 6, tissue-engaging structure 150 engages with tissue 58 which defines incision 56, thereby securing or aiding to secure surgical apparatus 124 within incision 56. Tissue-engaging structure 150 may include annular ridges 152 and a channel 154 defined between ridges 152. When the first length $l_1$ of member 126 is received within slot of adjusting portion 138, channel 154 slidably receives projection 134 therein. The engagement of channel 154 with projection 134 provides guidance as the first length $l_1$ slides through slot 136 and provides added torsional stability and rigidity to apparatus 124. Apparatus 124 may also include a locking mechanism for locking or temporarily retaining the first length $l_1$ of member 126 at a desired positioned within slot 136 so that apparatus 124 maintains a desired size during a surgical procedure.

The exemplary surgical apparatus of the present invention may be utilized in any number of surgical procedures in which the retraction of tissue, that is, the formation of an opening, would be advantageous. For example, one of the exemplary applications of the surgical apparatus is in heart valve replacement surgery. As surgical procedures become beneficially more minimally invasive (that is, less traumatic to the patient), medical products used in such procedures need to provide surgeons with tools enabling them to perform surgical procedures less invasively. This is particularly true in heart valve replacement surgery. An exemplary application of the surgical apparatus of the present invention used in heart valve replacement surgery will be discussed below.

Figure 20:
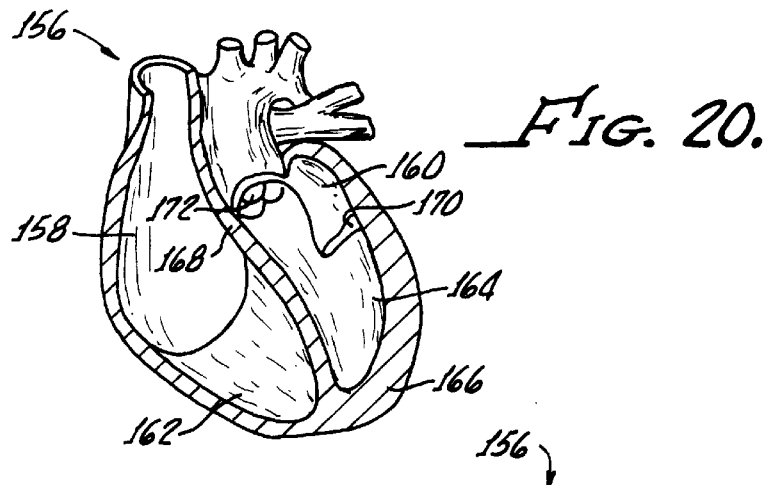
FIG. 20 is a partial cross-sectional view of a heart from an anterior perspective.

Referencing FIG. 20, a heart 156, which is shown in an anterior partial section, has four chambers, including a right atrium 158, a left atrium 160, a right ventricle 162, and a left ventricle 164. Tissue of the heart 156 includes myocardium 166, which is essentially the muscle of the heart, and a septum 168 which separates the right chambers of the heart from the left chambers. (Specifically, the muscular ventricular septum separates the ventricles, and the membranous septum generally separates the atria.) Valves define openings to the chambers and include a mitral valve 170 positioned between the left atrium 160 and the left ventricle 164 and an aortic valve 172 positioned between the left ventricle 164 and the aorta.

Figure 21:
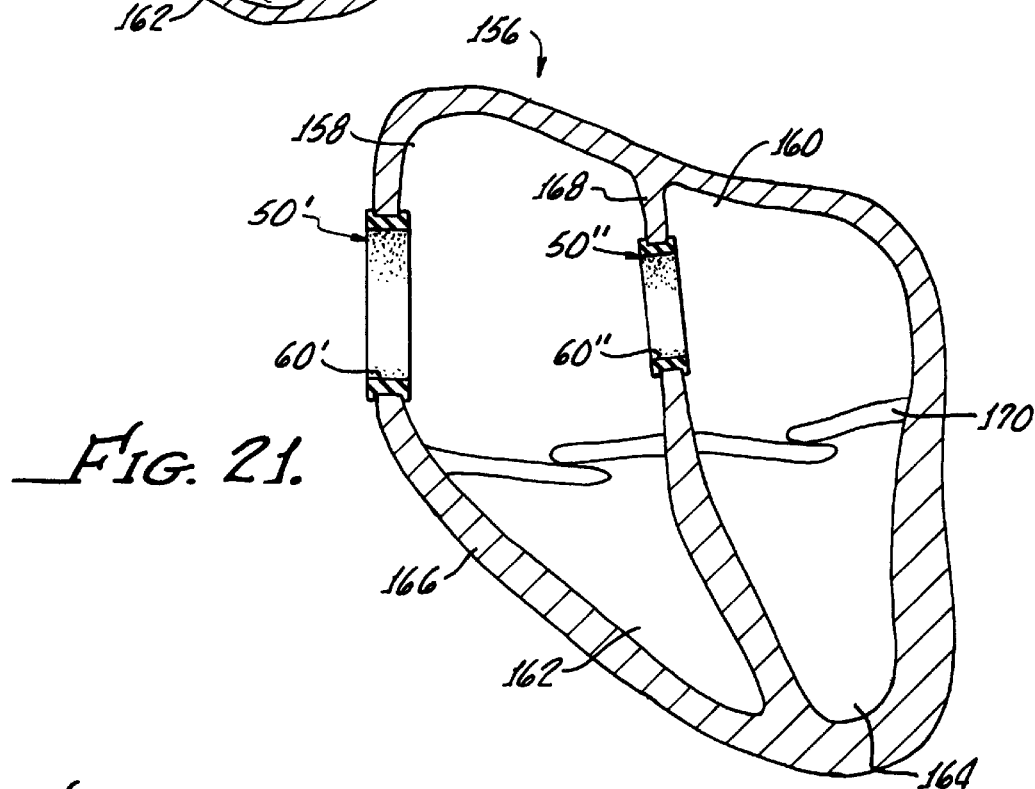
FIG. 21 is a schematic cross-sectional view of a heart, illustrating apparatus of the present invention in a cardiac surgical procedure.

One of the most common valve replacement surgeries is the replacement of the mitral valve 170. Although different procedures exists for replacing the mitral valve 170, one procedure involves accessing the mitral valve 170 through the right and left atria 158, 160, respectively. This is due to the physiological position of the heart 156 within the chest cavity of a patient, with the right chambers of the heart being anteriorly positioned and the left chambers being posteriorly positioned. With reference to FIG. 21, to perform this mitral valve replacement surgery, after accessing the heart 156, a surgeon makes an incision through the myocardium 166 to provide access to the right atrium 158. A surgical apparatus in accordance with the present invention, for example, apparatus 50', may then be positioned within incision and expanded as described above (see FIGS. 3B and 3C) to define an opening 60'. An incision may then be made in the septum 168 between the right atrium 158 and the left atrium 160, with another apparatus 50" positioned within this incision, thereby defining opening 60" between the atria. Accordingly, the surgeon may now access the mitral valve 170 through openings 60', 60" and perform procedures required to replace the valve.

In addition to the surgical procedure described above, the utilization of surgical apparatus of the present invention is widely applicable to many other procedures in which any type of tissue may be retracted. Further, the surgical apparatus need not necessarily be positioned within an incision but may be placed adjacent, for example, an organ so that the outward radial force applied by the surgical apparatus may urge or retract the organ from obstructing a surgical field. In addition, rather than working through the opening defined in the aperture when in an expanded condition, the surgical apparatus may be positioned in or near an incision so that a surgeon is able to work adjacent to the outer periphery of the members, that is, in a opening defined by the outer periphery of the member and the surrounding tissue. In a commercial embodiment, the surgical apparatus may be included in kits which include other related items for use in a particular procedure. The member of the surgical apparatus may include structure such as sewing holes to aid the surgeon in retaining tissue. The surgical apparatus may be configured so as to be "specialized" for a particular type of incision or tissue, particularly the tissue-engaging structures. The surgical apparatus may be of varying size (including thickness, depth, width, height, diameter, etc.). Further, the tissue surgical apparatus may include features designed to aid the surgeon during the procedure.

Figure 22:
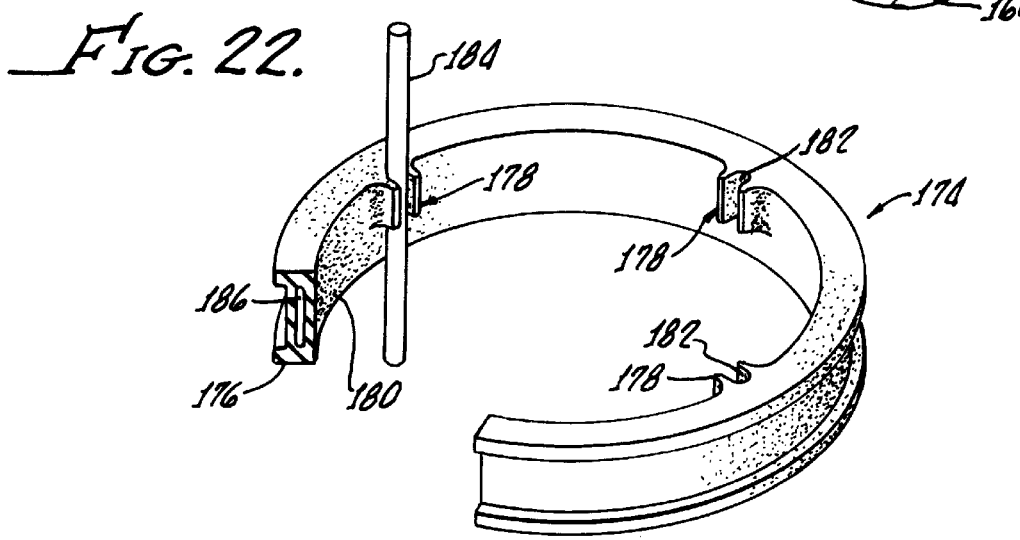
FIG. 22 is a perspective view of an apparatus in accordance with yet another embodiment of the present invention, with a portion of the surgical apparatus shown in cross section.

In this regard, reference is made to FIG. 22 which illustrates an exemplary embodiment of a surgical apparatus 174 including a member 176. A retaining structure 178 or, more preferably, a plurality of retaining structures 178 are disposed around an inner periphery 180 of member 176. Retaining structures 178 may be configured as clips including a central channel 182 for receiving a surgical implement 184 or leads coupled to external surgical apparatus which a may be used during an operation. Retaining structures 178 are preferably made from a resilient material so as to temporarily retain the surgical implements 184, and may be integral with or attached to member 176. Body member 176 may have an inner channel 186 formed therein. Inner channel 186 facilitates the compression of member 176 and may be used to house leads attached to a light source (see FIGS. 7 and 8). In addition, inner channel 186 may house a spring apparatus which biases member 176 to assume an expanded position. With further reference to FIGS. 9 and 10, inner channel 186 may house luminescent structure 80, with inner periphery 180 being translucent.

As mentioned, the surgical apparatus of the present invention may be made from a resilient bio-compatible material. Examples of such material which may be used in the manufacture of the surgical apparatus include polyacetal, polycarbonate, polyester, polyethylene, polyphenylsulfone, polypropylene, polysulfone, polyurethane, polyvinyl chloride, and silicone. In addition, apparatus 124 illustrated in FIGS. 17 and 18 may be made from materials including stainless steel and titanium. Rather than making, for example, apparatus 50 from a solid resilient material, apparatus 50 may include an inner or imbedded spring apparatus (as mentioned above) which is biased to an expanded condition. Such a spring apparatus may be made from stainless steel or titanium.

Those skilled in the art will understand that the embodiments of the present invention described above exemplify the principles of the invention and do not limit the scope of the invention to those embodiments of the surgical apparatus specifically illustrated in the drawings and described above. The exemplary embodiments provide a foundation from which numerous alternatives and modifications may be made, which alternatives and modifications are also within the scope of the present invention as defined in the appended claims.

What is claimed is:

1. A surgical apparatus for retracting animal tissue, said apparatus comprising:
    a resilient, deformable member having a loop shape defining an interior surface and an exterior surface, and being deformable about a region of said member having less resiliency than other regions of said member between a compressed insertion position wherein opposing regions of said interior surface contact each other when said member is fully compressed and an expanded tissue-supporting position.

2. The apparatus of claim 1 wherein said member is provided with a tissue-engaging structure disposed about said exterior surface.

3. The apparatus of claim 1 further comprising a light source disposed on said member.

4. An apparatus according to claim 1, further comprising diametrically-opposed flex portions having less resiliency than remaining portions of said member to facilitate folding and compression of said member at said flex portions.

5. A surgical apparatus for retracting animal tissue, said apparatus comprising:
    a resilient, deformable member having a loon shape defining an interior surface and an exterior surface, said member being provided with at least one flex portion having less resiliency than remaining portions of said member and being deformable about said at least one flex portion between a compressed insertion position wherein opposing portions of said interior surface contact each other when said member is fully compressed and an expanded tissue-supporting position.

6. A surgical apparatus for retracting heart tissue, said apparatus comprising:
    a member having an inner periphery and an outer periphery, and
    an aperture definable within said inner periphery;
    said member being adjustable between a compressed condition in which said aperture is substantially closed and an expanded condition in which said aperture is substantially open and has sufficient strength to keen said heart tissue in a substantially atraumatic retracted position.

7. The surgical apparatus of claim 6 wherein said member is resiliently biased to said expanded condition.

8. The surgical apparatus of claim 7 wherein said member is provided with at least one flex portion having less resiliency than remaining portions of said member.

9. The surgical apparatus of claim 8 wherein said flex portion is a slot.

10. The surgical apparatus of claim 8 wherein said member is substantially circular and is provided with a pair of diametrically opposed flex portions.

11. The surgical apparatus of claim 6 wherein said member is provided with a tissue-engaging structure on said outer periphery.

12. The surgical apparatus of claim 11 wherein said tissue-engaging structure includes an annular ridge.

13. The surgical apparatus of claim 6 further comprising a light source disposed on said member.

14. The surgical apparatus of claim 13 wherein said light source includes a light-emitting element coupled to an external power source.

15. The surgical apparatus of claim 13 wherein said light source is chemiluminescent.

16. The surgical apparatus of claim 15 wherein said chemiluminescent light source comprises:
    a housing having a first chamber, a divider, a second chamber and a translucent wall defining at least a portion of said inner periphery of said member; and
    a first chemical solution and a second chemical solution respectively received within said first chamber and said second chamber, said chemical solutions being chemiluminescent when mixed together.

17. The surgical apparatus of claim 16 wherein said divider is breakable when said member is in said compressed condition.

18. AThe surgical apparatus of claim 6 further comprising a mechanical adjuster for moving said member between said compressed condition and said expanded condition.

19. The surgical apparatus of claim 18 wherein:
    said member is an open loop having a first and second opposing ends, and a plurality of notches formed along a first length of said member adjacent to said first end; and
    said mechanical adjuster portion is disposed on said second end of said member and includes:
        a slot for slidably receiving said first end and said first length of said member thereby defining said aperture; and
        a toothed drive for engaging said plurality of notches.

20. The surgical apparatus of claim 6 further comprising a retaining structure disposed on said member for retaining an additional surgical apparatus.

21. A method for retracting tissue, said method comprising the steps of:
    forming an incision in the tissue; compressing the surgical apparatus of claim 6 and positioning said surgical apparatus in said incision; and
    expanding said surgical apparatus within said incision to open said aperture.

22. A method for retracting heart tissue, said method comprising the steps of:
    forming an incision through said heart tissue;
    positioning the surgical apparatus of claim 6 in said incision;

expanding said surgical apparatus within said incision to form an opening in said heart tissue.

23. The method of claim 22 further comprising the additional step of:
compressing said surgical apparatus prior to said positioning step.

24. A device for retracting heart tissue comprising:
a body member having a closed-loop shape;
said body member being deformable between a compressed condition and an expanded condition;
said body member having sufficient resilience to substantially atraumatically retract heart tissue when said body member is positioned within a surgical field;
said body member having sufficient flexibility to enable opposite inside interior surfaces of said body member to come into contact with each other when said body member is fully compressed by a human hand.

25. The apparatus of claim 24 wherein said member is provided with a tissue-engaging structure disposed about said exterior surface.

26. The apparatus of claim 24 further comprising a light source disposed on said member.

27. A device according to claim 24 further comprising diametrically-opposed flex portions having less resiliency than remaining portions of said member to facilitate folding and compression of said member at said flex portions.

28. A surgical apparatus for retracting tissue, said apparatus comprising:
a member having an inner periphery and an outer periphery, said member being resiliently biased to an expanded condition and provided with at least one flex portion having less resiliency than remaining portions of said member;
an aperture definable within said inner periphery; and
said member being adjustable about said at least one flex portion between a compressed condition in which said aperture is substantially closed and said expanded condition in which said aperture is substantially open.

29. The surgical apparatus of claim 28 wherein said flex portion is a slot.

30. The surgical apparatus of claim 28 wherein said member is substantially circular and is provided with a pair of diametrically opposed flex portions.

31. The surgical apparatus of claim 28 wherein said member is provided with a tissue-engaging structure on said outer periphery.

32. The surgical apparatus of claim 31 wherein said tissue-engaging structure includes an annular ridge.

33. The surgical apparatus of claim 28 further comprising a light source disposed on said member.

34. The surgical apparatus of claim 33 wherein said light source includes a light-emitting element coupled to an external power source.

35. The surgical apparatus of claim 33 wherein said light source is chemiluminescent.

36. The surgical apparatus of claim 35 wherein said chemiluminescent light source comprises:
a housing having a first chamber, a divider a second chamber and a translucent wall defining at least a portion of said inner periphery of said member; and
a first chemical solution and a second chemical solution respectively received within said first chamber and said second chamber, said chemical solutions being chemiluminescent when mixed together.

37. The surgical apparatus of claim 36 wherein said divider is breakable when said member is in said compressed condition.

38. The surgical apparatus of claim 28 further comprising a mechanical adjuster for moving said member between said compressed condition and said expanded condition.

39. The surgical apparatus of claim 38 wherein:
said member is an open loop having a first and second opposing ends, and a plurality of notches formed along a first length of said member adjacent to said first end; and
said mechanical adjuster is disposed on said second end of said member and includes:
a slot for slidably receiving said first end and said first length of said member thereby defining said aperture; and
a toothed drive for engaging said plurality of notches.

40. The surgical apparatus of claim 28 further comprising a retaining structure disposed on said member for retaining an additional surgical apparatus.

41. An apparatus according to claim 28, wherein said apparatus includes diametrically-opposed flex portions having less resiliency than remaining portions of said member to facilitate folding and compression of said member at said flex portions.

42. A method for retracting heart tissue, said method comprising the steps of;
forming an incision in the tissue;
compressing the surgical apparatus of claim 28, and positioning said surgical apparatus in said incision; and
expanding said surgical apparatus within said incision to form an opening in said heart tissue.

43. A method for retracting heart tissue, said method comprising the steps of:
forming an incision through said heart tissue;
positioning the surgical apparatus of claim 28 in said incision; and
expanding said surgical apparatus within said incision to form an opening in said heart tissue.

44. The method of claim 43 further comprising the additional step of:
compressing said surgical apparatus prior to said positioning step.

45. A surgical apparatus for retracing tissue, said apparatus comprising:
a member having an inner periphery and an outer periphery;
an aperture definable within said inner periphery;
a light source disposed on said member, said light source being chemiluminescent; and
said member being adjustable between a compressed condition in which said aperture is substantially closed and an expanded condition in which said aperture is substantially open.

46. The surgical apparatus of claim 45 wherein said member is resiliently biased to an expanded condition.

47. The surgical apparatus of claim 46 wherein said member is provided with at least one flex portion having less resiliency than remaining portions of said member.

48. The surgical apparatus of claim 47 wherein said flex portion is a slot.

49. The surgical apparatus of claim 47 wherein said member is substantially circular and is provided with a pair of diametrically opposed flex portions.

50. The surgical apparatus of claim 45 wherein said member is provided with a tissue-engaging structure on said outer periphery.

51. The surgical apparatus of claim 50 wherein said tissue-engaging structure includes an annular ridge.

52. The surgical apparatus of claim 45 wherein said light source includes a translucent wall.

53. The surgical apparatus of claim 45 wherein said chemiluminescent light source comprises:
   a housing having a first chamber, a divider, a second chamber and a translucent wall defining at least a portion of said inner periphery of said member; and
   a first chemical solution and a second chemical solution respectively received within said first chamber and said second chamber, said chemical solutions being chemiluminescent when mixed together.

54. The surgical apparatus of claim 53 wherein said divider is breakable when said member is in said compressed condition.

55. The surgical apparatus of claim 45 further comprising a mechanical adjuster for moving said member between said compressed condition and said expanded condition.

56. The surgical apparatus of claim 55 wherein:
   said member is an open loop having a first and second opposing ends, and a plurality of notches formed along a first length of said member adjacent to said first end; and
   said mechanical adjuster is disposed on said second end of said member and includes:
      a slot for slidably receiving said first end and said first length of said member thereby defining said aperture; and
      a toothed drive for engaging said plurality of notches.

57. The surgical apparatus of claim 45 further comprising a retaining structure disposed on said member for retaining an additional surgical apparatus.

58. A method for retracting heart tissue, said method comprising the steps of:
   forming an incision in the tissue;
   compressing the surgical apparatus of claim 45, and positioning said surgical apparatus in said incision; and
   expanding said surgical apparatus within said incision to form an opening in said heart tissue.

59. A method for retracting heart tissue, said method comprising the steps of:
   forming an incision through said heart tissue;
   positioning the surgical apparatus of claim 45 in said incision; and
   expanding said surgical apparatus within said incision to form an opening in said heart tissue.

60. The method of claim 59 further comprising the additional step of:
   compressing said surgical apparatus prior to said positioning step.

61. A surgical apparatus for retracting tissue, said apparatus comprising:
   a member having an inner periphery and an outer periphery;
   an aperture definable within said inner periphery;
   a mechanical adjuster for moving said member between said compressed condition and said expanded condition, said member being an open loop having a first and second opposing ends, and a plurality of notches formed along a first length of said member adjacent to said first end; and
   said mechanical adjuster being disposed on said second end of said member and including:
      a slot for slidably receiving said first end and said first length of said member thereby defining said aperture;
      a toothed drive for engaging said plurality of notches; and
   said member being adjustable between a compressed condition in which said aperture is substantially closed and an expanded condition in which said aperture is substantially open and applies an outward radial force to said tissue.

62. The surgical apparatus of claim 61 wherein said member is resiliently biased to an expanded condition.

63. The surgical apparatus of claim 62 wherein said member is provided with at least one flex portion having less resiliency than remaining portions of said member.

64. The surgical apparatus of claim 63 wherein said flex portion is a slot.

65. The surgical apparatus of claim 63 wherein said member is substantially circular and is provided with a pair of diametrically opposed flex portions.

66. The surgical apparatus of claim 61 wherein said member is provided with a tissue-engaging structure on said outer periphery.

67. The surgical apparatus of claim 66 wherein said tissue-engaging structure includes an annular ridge.

68. The surgical apparatus of claim 61 further comprising a light source disposed on said member.

69. The surgical apparatus of claim 68 wherein said light source includes a light-emitting element coupled to an external power source.

70. The surgical apparatus of claim 68 wherein said light source is chemiluminescent.

71. The surgical apparatus of claim 70 wherein said chemiluminescent light source comprises
   a housing having a first chamber, a divider, a second chamber and a translucent wall defining at least a portion of said inner periphery of said member; and
   a first chemical solution and a second chemical solution respectively received within said first chamber and said second chamber, said chemical solutions being chemiluminescent when mixed together.

72. The surgical apparatus of claim 71 wherein said divider is breakable when said member is in said compressed condition.

73. The surgical apparatus of claim 61 further comprising a retaining structure disposed on said member for retaining an additional surgical apparatus.

74. A method for retracting heart tissue, said method comprising the steps of:
   forming an incision in the tissue;
   compressing the surgical apparatus of claim 61, and positioning said surgical apparatus in said incision; and
   expanding said surgical apparatus within said incision to form an opening in said heart tissue.

75. A method for retracting heart tissue, said method comprising the steps of:
   forming an incision through said heart tissue;
   positioning the surgical apparatus of claim 61 in said incision, and
   expanding said surgical apparatus within said incision to form an opening in said heart tissue.

76. The method of claim 75 further comprising the additional step of:
   compressing said surgical apparatus prior to said positioning step.

77. A method for retracting tissue, said method comprising the steps of:
   forming an incision in the tissue;

compressing the surgical apparatus of claim 61, and positioning said surgical apparatus in said incision; and expanding said surgical apparatus within said incision to form an opening in said heart tissue.

78. A method for retracting heart tissue, said method comprising the steps of:

forming an incision through said heart tissue;

positioning a surgical apparatus for retracting tissue, said apparatus comprising a member having an inner periphery and an outer periphery and an aperture definable within said inner periphery, said member being adjustable between a compressed condition in which said aperture is substantially closed and an expanded condition in which said aperture is substantially open, in said incision; and expanding said surgical apparatus within said incision to form an opening in said heart tissue.

79. The method of claim 78 wherein said member is resiliently biased to an expanded condition.

80. The method of claim 79 wherein said member is provided with at least one flex portion having less resiliency than remaining portions of said member.

81. The method of claim 80 wherein said flex portion is a slot.

82. The method of claim 80 wherein said member is substantially circular and is provided with a pair of diametrically opposed flex portions.

83. The method of claim 78 wherein said member is provided with a tissue-engaging structure on said outer periphery.

84. The method of claim 83 wherein said tissue-engaging structure includes an annular ridge.

85. The method of claim 78 further comprising a li-ht source disposed on said member.

86. The method of claim 85 wherein said light source includes a light-emitting element coupled to an external power source.

87. The method of claim 85 wherein said light source is chemiluminescent.

88. The method of claim 87 wherein said chemiluminescent light source comprises:

a housing having a first chamber, a divider, a second chamber and a translucent wall defining at least a portion of said inner periphery of said member; and a first chemical solution and a second chemical solution respectively received within said first chamber and said second chamber, said chemical solutions being chemiluminescent when mixed together.

89. The method of claim 88 wherein said divider is breakable when said member is in said compressed condition.

90. The method of claim 78 further comprising a mechanical adjuster for moving said member between said compressed condition and said expanded condition.

91. The method of claim 90 wherein;

said member is an open loop having a first and second opposing ends, and a plurality of notches formed along a first length of said member adjacent to said first end; and said mechanical adjuster is disposed on said second end of said member and includes:

a slot for slidably receiving said first end and said first length of said member thereby defining said aperture; and a toothed drive for engaging said plurality of notches.

92. The method of claim 74 further comprising a retaining structure disposed on said member for retaining an additional surgical apparatus.

93. The method of claim 78 further comprising the additional step of:

compressing said surgical apparatus prior to said positioning step.

* * * * *

UNITED STATES PATENT AND TRADEMARK OFFICE
CERTIFICATE OF CORRECTION

PATENT NO. : 6,162,172
DATED : December 19, 2000
INVENTOR(S) : Delos M. Cosgrove, et at.

It is certified that error appears in the above-identified patent and that said Letters Patent is hereby corrected as shown below:

<u>Claims,</u>
<u>Claim 6,</u>
Line 9, replace "keen" with "keep."

<u>Claim 85,</u>
Line 1, replace "li-hit" with "light."

<u>Claim 92,</u>
Line 1, replace "74" with "78."

Signed and Sealed this

Twenty-third Day of October, 2001

Attest:

*Nicholas P. Godici*

NICHOLAS P. GODICI
*Attesting Officer*     *Acting Director of the United States Patent and Trademark Office*